United States Patent [19]

Nörthemann et al.

[11] 4,449,266
[45] May 22, 1984

[54] TOOTHBRUSH WITH TWO SEGMENTS OF BRISTLES

[76] Inventors: Karl-Heinz Nörthemann, Ringstrasse 18, D-3501 Schauenburg, 4; Heinrich Krahn, Schönfelderstrasse 4, D-3507 Baunatal 5, both of Fed. Rep. of Germany

[21] Appl. No.: 356,409

[22] Filed: Mar. 9, 1982

Related U.S. Application Data

[60] Continuation-in-part of Ser. No. 946,835, Sep. 27, 1978, abandoned, which is a division of Ser. No. 684,184, Jul. 1, 1976, Pat. No. 4,131,967.

[51] Int. Cl.³ ............................................. A46B 9/04
[52] U.S. Cl. .................................................. 15/167 A
[58] Field of Search ................. 15/167 R, 167 A, 110, 15/143 R

[56] References Cited

U.S. PATENT DOCUMENTS

| 482,788 | 4/1937 | Dehn . |
| 569,870 | 10/1896 | Hamilton . |
| 1,353,780 | 9/1920 | Mueller . |
| 1,389,624 | 9/1921 | Carroll . |
| 2,077,392 | 4/1937 | Boyd . |
| 2,263,360 | 11/1941 | Karshmer . |
| 3,067,447 | 12/1962 | Birch . |

FOREIGN PATENT DOCUMENTS

| 229389 | 6/1943 | Fed. Rep. of Germany . |
| 707843 | 12/1930 | France . |
| 855253 | 5/1939 | France . |
| 911243 | 6/1945 | France . |
| 1075171 | 8/1952 | France . |
| 1230365 | 7/1959 | France . |
| 332091 | 10/1958 | Switzerland . |
| 247005 | 2/1926 | United Kingdom . |

*Primary Examiner*—Peter Feldman
*Attorney, Agent, or Firm*—Armstrong, Nikaido, Marmelstein, Kubovcik

[57] ABSTRACT

A toothbrush having an elongated handle, the handle defining a center plane containing the longitudinal axis. A pair of bristle-bearing segments, each segment containing a plurality of bristles mounted therein, is connected to the handle by a pair of short arms. The arms, bristle-bearing segments, and the handle form a fork having two prongs, each prong containing one bristle-bearing segment and one connecting arm. The prongs are located on opposite sides of the first center plane and below a second center plane perpendicular to the first center plane. The bristle-bearing segments have mutually facing inside surfaces sloping toward each other in a gable-manner and intersect above the upper side of the handle at a first angle of less than 55°. The free ends of the bristles bound a gap and define side surfaces sloping in a gable-manner toward each other intersecting above the gap and at a second angle which is less than the first angle.

16 Claims, 25 Drawing Figures

TOOTHBRUSH WITH TWO SEGMENTS OF BRISTLES

The application is a continuation-in-part application of U.S. patent application Ser. No. 946,835 filed Sept. 27, 1978, now abandoned which in turn is a divisional application of U.S. patent application Ser. No. 684,184, filed July 1, 1976, now U.S. Pat. No. 4,131,967 issued Jan. 2, 1979.

When a toothbrush with a single segment of bristles is used, only the front or the rear tooth areas can be cleaned in one cleansing stroke. The same considerations apply to the care and massaging of the gums. As a result the drawback is incurred that the front and well visible tooth surfaces are cleaned preferentially while the rear, less visible tooth surfaces are being neglected. Toothbrushes with two bodies of bristles are known for the purpose of remedying this drawback, by means of which the front and rear areas of the teeth and gums can be cleaned or massaged in a single cleaning action.

For many reasons, no one of the known toothbrushes of this type was able to win wide acceptance. Most of all, no one of the known toothbrushes takes enough into account the positions and the arrangements of the teeth in the human mouth the space available in the mouth for dental care, and the methods of manufacture on an industrial scale required for such toothbrushes.

A known toothbrush (U.S. Pat. No. 2,077,392) comprises two segments of bristles arranged in a U-shape, the bottom sides of the handle and of the bristle body being in one plane. Such a toothbrush is more of a hindrance than useful in the mouth and presents difficulties in manufacture because the bristles must be fastened to the bristle segments using a flexible support. In other toothbrushes (Swiss Pat. No. 332,091; French Pat. No. 1,075,171; U.S. Pat. No. 2,263,360), the bristle bodies do in fact form an angle of about 90°, whereby the bristles can be inserted conventionally in one automatic operational stage. However so large an angle on one hand requires the inserted bristles to be also arranged at an angle of about 90°, whereby the toothbrush can only be used for cleaning the front or rear tooth surfaces and a rotation by 90° is needed to clean any other tooth surface. On the other hand the design of the toothbrush results in an unpleasantly large width. Furthermore the freedom of motion of the toothbrush within the mouth is hampered by the arm mounted directly above the bristle segments. A further known toothbrush (French Pat. No. 1,075,171) comprises segments of bristles bent into approximate arcs of circles, as a result of which the total width is excessive and it is impossible for the bristles to reach the gums. Moreover the toothbrush head must be made either from a malleable metal or in two parts, which is undesirable. As regards a plurality of further known toothbrushes (U.S. Pat. Nos. 569,870; 1,353,780; 1,389,624; French Pat. Nos. 855,253; 911,243; Swiss Pat. No. 229,389 and British Pat. No. 247,005), the bristle bodies do bound a slit which is open at the top and bottom, whereby their freedom of motion within the mouth is facilitated. However in these toothbrushes the bristle segments are joined by means of relatively long elastic connecting segments with the handle on one side, so that during the cleaning action the bristles can transmit only a relatively low and most of the time inadequate force. On the other hand the bristles are arranged at least in part so disadvantageously that a simultaneous cleaning or massaging of the front and rear tooth areas or gums is hardly feasible. In addition as regards some of these toothbrushes (U.S. Pat. No. 569,870; British Pat. No. 247,005), some of the bristles must be made so long for the purpose of achieving a narrow, wedge-shaped slit, that they act in any event as an artist's brush but not as cleaning brush when cleaning the teeth.

It is the object of the invention to provide a toothbrush for the care of human teeth with two segments of bristles which take into account the positions of the teeth in the mouth by a corresponding arrangement and dimensioning of the bristles. Another object is to minimize as much as possible the outside dimensions of the toothbrush head formed by the two bristle segments, so that the cleaning procedure shall not be hampered by an excessive size of the head, and this without thereby simultaneously reducing the force of cleaning in any appreciable manner. Lastly it is the object of the invention to provide a method making possible an extensively automated and hence industrial production of toothbrushes with two segments of bristles.

These and other objects of the invention are resolved by the toothbrush of the invention, which is made of a thermoplastically deforming plastic save the bristles. The toothbrush of the invention comprises an elongated handle with a front termination tapering toward the end away from the handle and with a rearward end, an upper side and a lengthwise axis, this handle also defining a conceptual center plane containing the lengthwise axis, and two segments of bristles which are so connected by short, thermoplastically deforming connecting arms to the end segment that the bristle segments, the connecting strips and the handle form a fork with two prongs each containing one segment of bristles and one connecting arm these prongs being located on opposite sides of the center plane and are essentially below another conceptual plane perpendicular to the center plane and containing the grip's lengthwise axis. The bristle segments evince inside surfaces shaped like a gable and facing each other, of which the conceptual extensions intersect above the upper edge of the handle at an angle less than 55° and which bear the bristles with free ends which bound a gap with conceptual gable-shaped inside surfaces facing each other, of which the conceptual extensions intersect above the gap but at a lesser angle than the inside surfaces of the bristle segment.

The invention is explained below in relation to the enclosed drawing and the embodiments, to which however the invention is not restricted.

Figures 1, 2, 4:
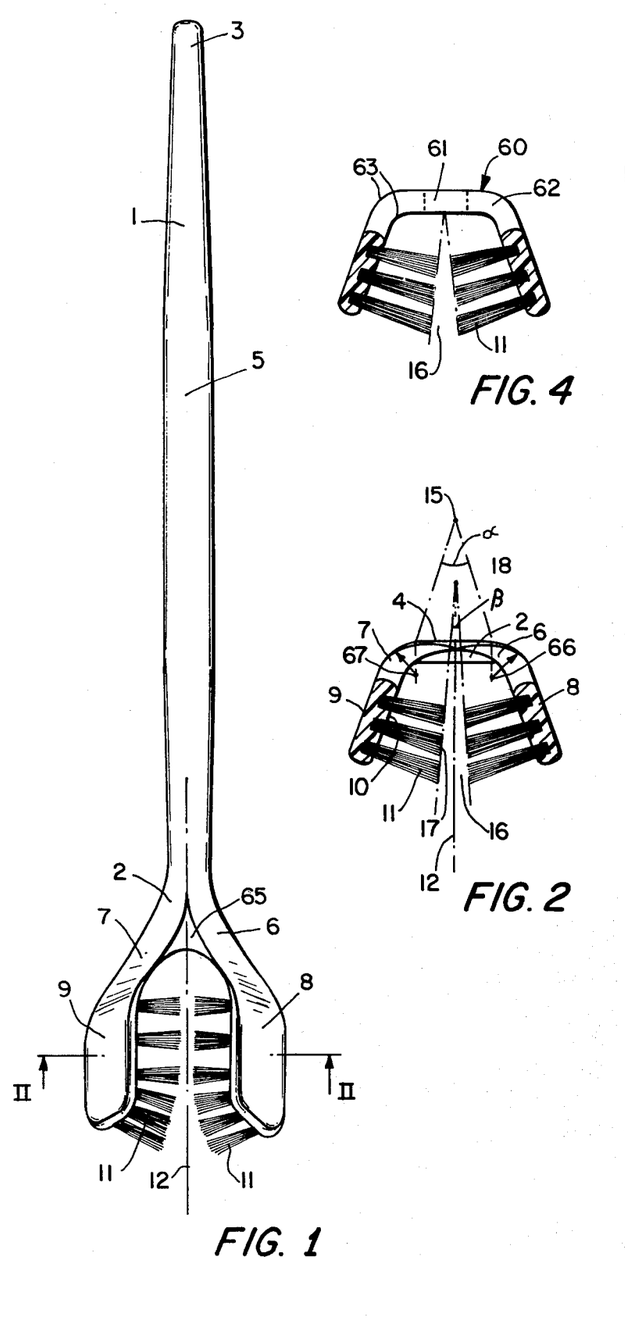
FIG. 1 is the top view of a toothbrush of the invention with two segments of bristles.
FIG. 2 is a section along the line II—II of FIG. 1 on an enlarged scale.
FIG. 4 is a section corresponding to FIG. 2 through a toothbrush lacking an essential feature of the invention.
Figure 3:
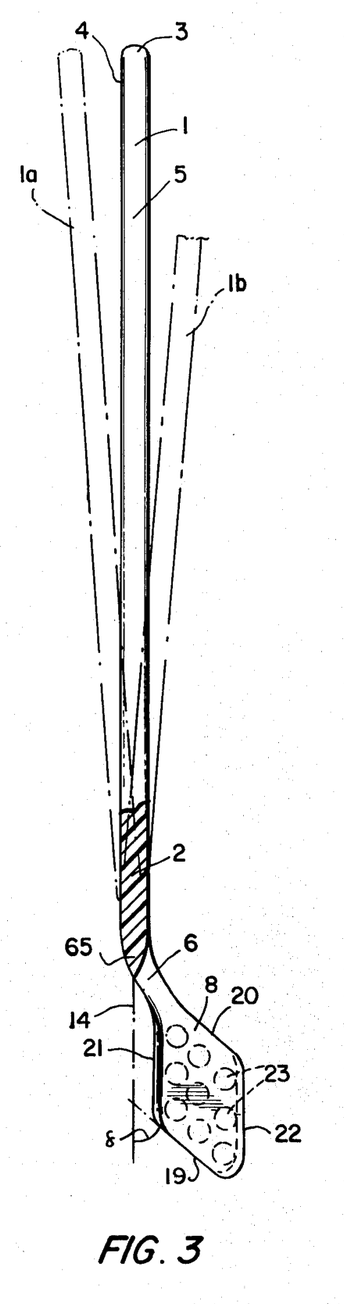
FIG. 3 is the side view of the toothbrush of FIG. 1.

The toothbrush shown in FIGS. 1 through 3 contains an elongated and essentially straight handle 1 comprising a front segment 2, a rear end 3, an upper side 4 and a lengthwise axis 5. The lengthwise axis is at the same time the axis of symmetry when a symmetrical handle 1 is used.

The rear segment 2 is joined by short connecting arms 6 and 7 with two bristle segments 8 and 9, which comprise mutually facing inside surfaces 10 to which are mounted bristles in the form of bundles 11. The connection arm 6, bristle segment 8 and the associated bristle bundles 11 are arranged on one side of a conceptual center plane 12 containing the lengthwise axis 5 and, in FIG. 1, perpendicular to the plane of the drawing. On the other hand the connection arm 7, bristle segment 9 and the bundles 11 of bristles fastened thereto are arranged on the opposite side of the center plane 12. Furthermore the handle 5, the connecting arms 6,7 and the bristle segments 8,9 form a fork of which the Y- or U-shaped prongs, when seen in topview in FIG. 1 consist each of one connection arm 6,7 and one bristle segment 8,9 these prongs being located on one hand one on each side of the center plane 12 and on the other hand per FIG. 3 essentially below another conceptual plane 14 which is perpendicular to the center plane 12 and contains the lengthwise axis 5 of the handle 1. This is the case regardless of the handle 1 drawn in solid lines terminating in the end segment 2 at the angle shown in FIG. 3 or whether it is so arranged with respect to this segment 2 as indicated by the handles 1a and 1b shown in dash-dot lines.

The inside surfaces 10 of the bristle segments 8 and 9 face each other as shown in FIG. 2 and incline toward each other in gable-, wedge- or V-shape manner, though of so little height that their mutually directed ends do not touch, rather the inside surfaces 10 bound a space of which the cross-section perpendicular to the center plane is essentially trapezoidal. Preferably the entire arrangement is symmetrical and the center plane 12 at the same time is the plane of symmetry. The conceptual extensions of the inside surfaces 10 shown in dashed lines in FIG. 2 intersect in a line which appears as a point 15 in FIG. 2 and which is located above the upper side 4 of the handle 1. The inside surfaces subtend an angle alpha of less than 55°.

The bristle bundles 11 fastened to the inside surfaces 10 are so arranged and/or cut (FIG. 2) that they bound a gap 16 and accordingly terminate at its conceptual side surfaces 17. The side surfaces 17 face each other and slant in gable-, wedge- or V-shape manner toward each other and due to the arrangement and the dimensioning of the inside surfaces 10 and bristle bundles 11 are of so slight a height that their mutually approaching ends do not touch, rather the gap 16 they define assumes a trapezoidal appearance in a cross-section perpendicular to the center plane 12. The extensions of the side surfaces 17 shown in dashed lines in FIG. 2 intersect in a line appearing as a point 18 in FIG. 2 and preferably located between the line 15 and the upper side 4 of the handle 1. The side surfaces 17 subtend an angle beta less than the angle alpha and preferably less than 15°.

As shown in FIG. 3, the bristle segments 8,9 each comprise a front edge 20, an upper side 21 and a lower side 22. The front edges 19 and preferably also the rear edges 20 subtend an acute angle gamma with the plane 14, preferably less than 60°, whereas the upper and lower sides 21 and 22 should be substantially parallel to the plane 14 so that the bristle segments 8 and 9 assume the shapes of diamonds.

The bristle bundles 11 are arranged at the inside surfaces 10 in several rows parallel to the upper and lower sides 21,22 and in columns, as indicated in particular in FIG. 3 by the circles 23. The bundles of bristles preferably are so mutually offset in adjacent rows that each bundle of bristles is arrayed at the gap between two bundles of an adjacent row. Such an arrangement will be especially obtained when arranging the bristle bundles in such a manner that four adjacent bristle bundles always form the four corners of a diamond.

Figure 5:
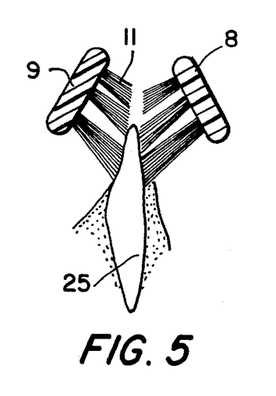
FIGS. 5 through 10 schematically show various positions of the toothbrush when being used.
Figure 6:
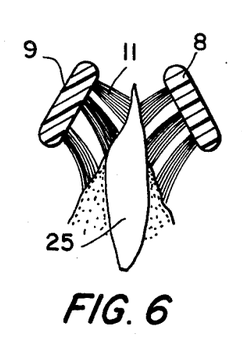
Figure 7:
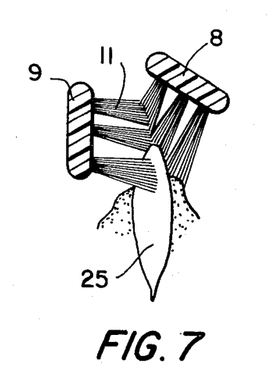
Figure 8:
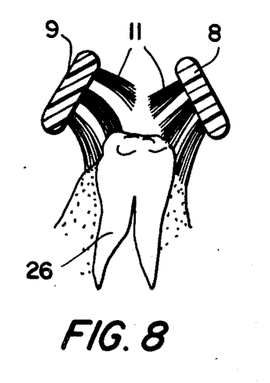
Figure 9:
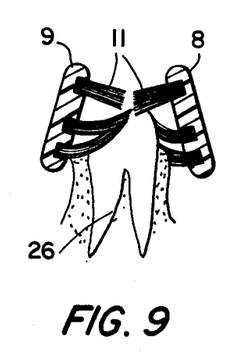
Figure 10:
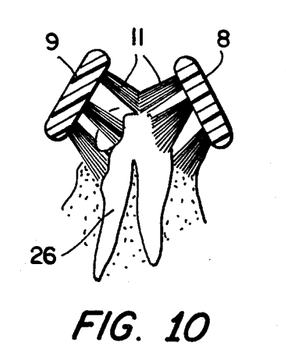

The toothbrush of the invention offers a plurality of advantages. Because the gap 16 bounded by the bristle bundles 11 and the fork formed by the bristle segments 8,9 are open at the top and at the bottom, the remaining parts of the toothbrush will hamper neither a reciprocating displacement nor a sideways pivoting of the bundles of bristles on the teeth being cleaned. The variously possible motions of the toothbrush when cleaning the teeth, the gaps between the teeth and the subcrestal pockets as well as when massaging the gums are shown in FIGS. 5 through 7 for the example of an incisor 25 and in FIGS. 8 through 10 for the example of a molar tooth 26 in schematic manner. Due to these motions, all films of solid and residual foods are removed, and also the blood supply to the gums is excited due to the massage. The dimensions listed for the gap 16 take into account the size and shape of average teeth in extensive manner.

Besides, the described shape of the toothbrush permits a comparatively large brushing surface at comparatively small outside dimensions. Because the lines 15 and 18 are arranged above the handle 1, the width especially of the head of the brush is comparatively slight and in a practical embodiment amounts to about 28 mm, measured perpendicularly to the center plane 12. The height of the brush too, measured from the lower sides 22 of the bristle segments to the extension of the upper side 4 of the handle 1 is about 20 mm, and comparatively slight. By suitably selecting the angles alpha and beta, one achieves furthermore that in operation the bristles will be nearly perpendicular to the tooth areas to be cleaned, whereby they can be highly effective in cleaning and massaging. Because the bundles of bristles are staggered with respect to the gaps of the adjoining rows, the bristle bundles 11 when in use extensively swing through freely, that is, they can be bent by their ends to any side without this motion being hampered by neighboring bundles of bristles. Lastly the obliquely arranged edge 19 of the bundles of bristles especially makes possible widely unhampered cleaning even of the rearmost molars.

An especially preferred method for the manufacture of the toothbrush described will be discussed below in relation to FIGS. 11 through 25.

First a molded article 28 is made, which comprises the handle 1 with the front piece 2 and the back piece 3 and the connection arms 6,7 and the bristle segments 8,9 and which is injection-molded in integral manner using a corresponding injection mold and a thermoplastically deforming plastic. Suitable plastics are thermoplastics, for instance that marketed by BASF under the tradename LURAN. The molded article consists of a flat body for instance 3 to 4 mm thick and assuming a Y- shape in topview as in FIG. 11, the handle 1 forming the long stem of the Y and the two short arms of the Y being formed each by one connection arm 6,7 and one bristle segment 8,9. The handle, the connection arms and the bristle segments share a central plane within the molded part 28 which is parallel to the plane of the FIG. 1.

When being injection-molded, the molded article 28 is simultaneously provided with a plurality of blind holes 29 (FIGS. 13,14) which shall receive the bundles 11 of bristles. Alternatively the blind holes 29 can be made by drilling or in some other way. According to FIG. 14 the molded article 28 is clamped into the clamping means of an implanting machine by means of which the bristle bundles 11 are sequentially introduced into the blind holes 29 indicated by arrows in FIG. 15. Machinery of this type is known and corresponds to that used in the manufacture of conventional toothbrushes. It is merely necessary to so modify the control electronics that the insertion device after the insertion of the bristles in the blind holes 29 of the one bristle segment shall jump to the other bristle segment to correspondingly insert the bristles there. After the bristle bundles 11 have been inserted, the insertion machine will drive one flat anchor 30 (FIGS. 11,13) into each of the blind holes 29 to fix the bristle bundles 11. The flat anchor 30 as a rule is a narrow metal plate with a length slightly exceeding the diameter of the blind holes 29 and with a height somewhat less than the depth of the blind holes. Thereby the flat anchors 30 somewhat dig into the material surrounding the blind holes 29 and thereafter are kept in these by a firm force-fit.

Figures 11, 14, 15, 16, 17:
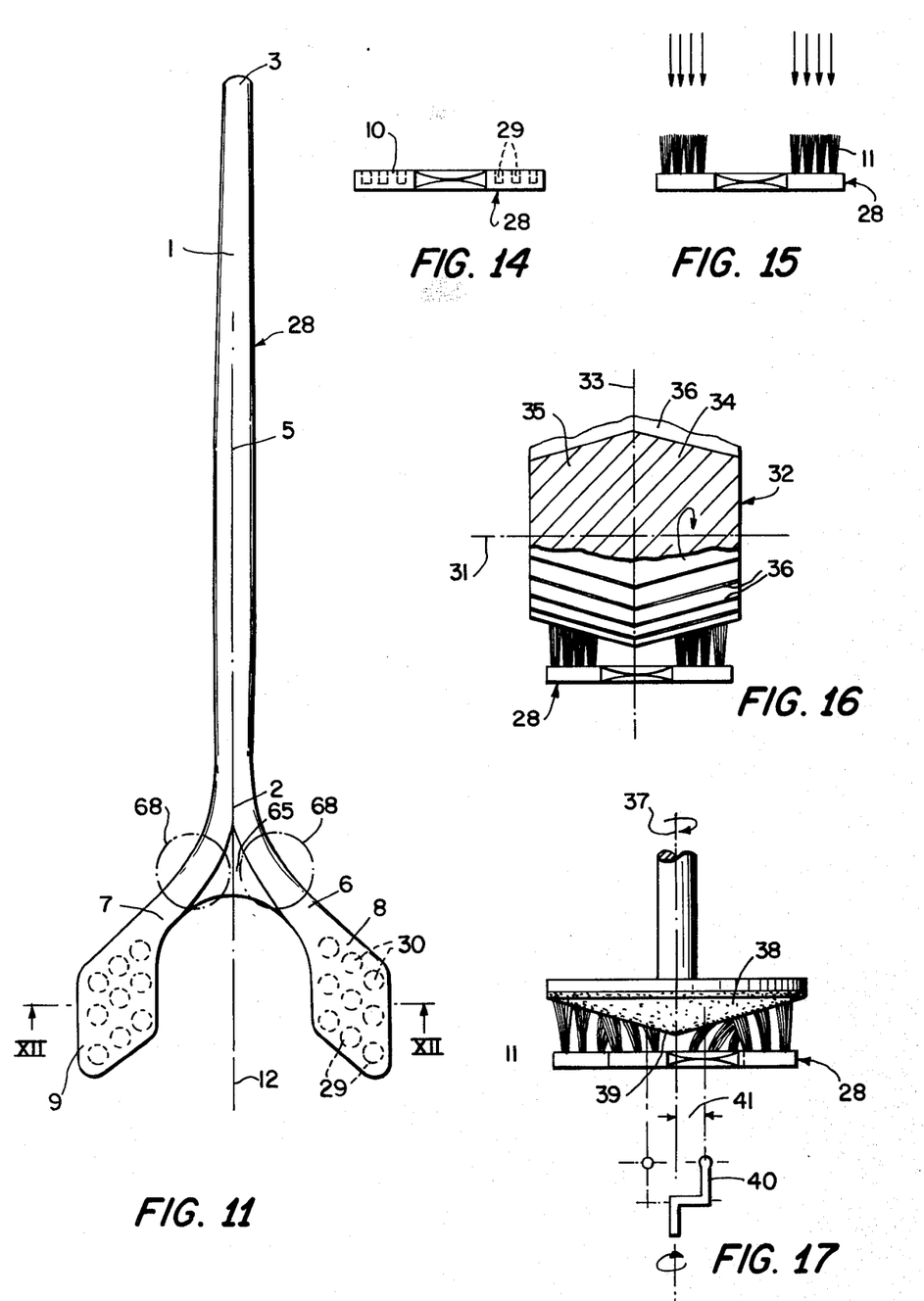
FIG. 11 is the top view of a molded article from which the toothbrush of FIGS. 1 through 3 will be shaped.
FIGS. 14 through 25 are various processing stages of the method used to manufacture the toothbrush of FIGS. 1 through 3, FIG. 24 showing on an enlarged scale the detail "B" of FIG. 23.
Figure 12:
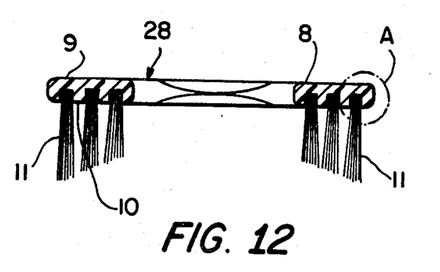
FIG. 12 is a section along the line XII—XII of FIG. 11.
Figure 13:
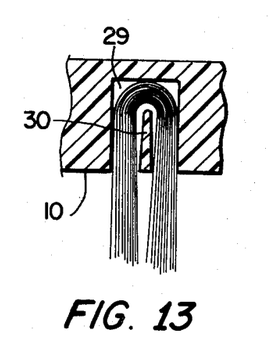
FIG. 13 is the detail "A" shown in FIG. 6 but on an enlarged scale.
Figure 18:
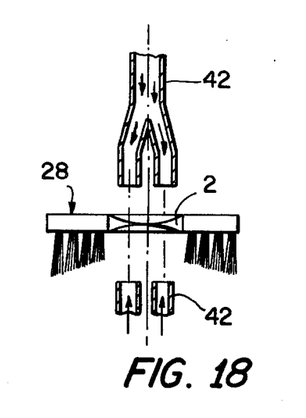
Figure 19:
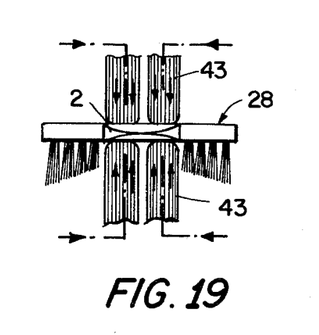

The free ends of the bristle bundles 11 are cut in the next processing stage by means of a profile cutter 11 shown schematically in FIG. 16 and comprising a head 32 rotatable about an axis 31 and consisting for instance of two frusto-conical sections 34 and 35 placed on each other by their wider bases along a center plane 33, steel cutting blades 36 or the like being inserted in their conical surfaces. The angle of inclination of the cutting blades 36 with respect to the axis of rotation 31 is so selected that the ends of the bristle bundles 36 will be cut obliquely in a pre-selected manner and receive the shape shown in FIG. 12.

Following cutting, the bundles of bristles are rounded off as indicated schematically in FIG. 17. To that end provision is made for instance of a grinding or cutting disk 38 rotating about an axis of rotation 37, of which the grinding or cutting surface 39 acting on the bristle ends is of a conical shape corresponding to the arrangement of the cutting blades 36. The disk 36 is driven additionally by means of a crank 40 or a cam indicated schematically in such a manner that the axis of rotation 37 is guided along a circle of radius 41 of which the central axis is parallel to the axis of rotation 37. Alternatively the clamping tool for the molded article 28 can be guided along such a circular path. Due to this arrangement the bristle ends are constantly guided along circles of radius 41 during the grinding procudure and accordingly they are being processed, ie rounded off from all sides.

The next processing stage begins with the molded article 28 being so softened in the area of its end segment 2 that the plastic material in view of its thermoplastic properties can be shaped. For that purpose the end segment 2 is subjected to heat treatment using hot air from schematically shown supply lines 42 (FIG. 18), or else it is treated ultrasonically by means of electrodes 43 and softened to malleability thereby.

Figure 20:
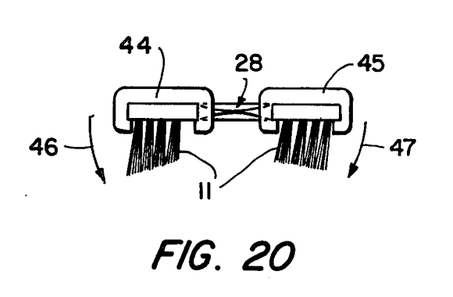
Figure 21:
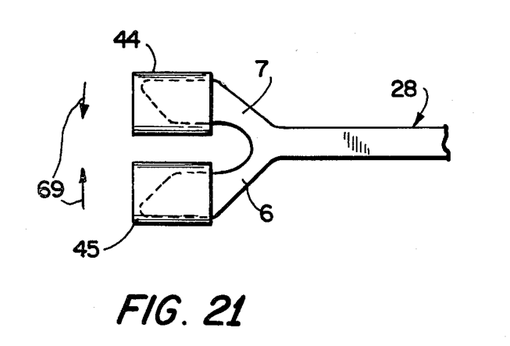
Figure 22:
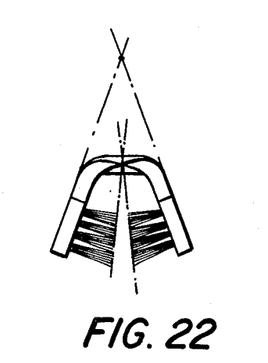

Thereupon the connection arms 6 and 7 are shaped for instance by constraining the bristle segments 8 and 9 to move by means of cam-controlled bending beams 44 and 45 (FIGS. 20,21) along a cam corresponding to the arrows 46 and 47 indicated in FIG. 20, until the cross-sectional shape corresponding to FIG. 2 and shown in FIG. 22 is obtained. As the softening of the plastic takes place in the area of the end segment 2 and in the immediate vicinity thereof, only the ends of the connection arms 6,7 adjoining the end segment will be practically shaped in the bending-, folding and forming procedure. The bending beams 44,45 are so guided that the fork described in relation to FIGS. 1 through 3 is obtained, of which the prongs consisting of the connection arms and the bristle segments are arranged below the lengthwise axis of the handle 5. It is possible by means of the cams acting on the bending beams 44 and 45 to very accurately set the desired end position of the bristle segments or of the bristle ends forming the gap 16. Thereupon the toothbrush is allowed to cool so as to freeze the shape obtained when shaping the connection arms.

Figure 23:
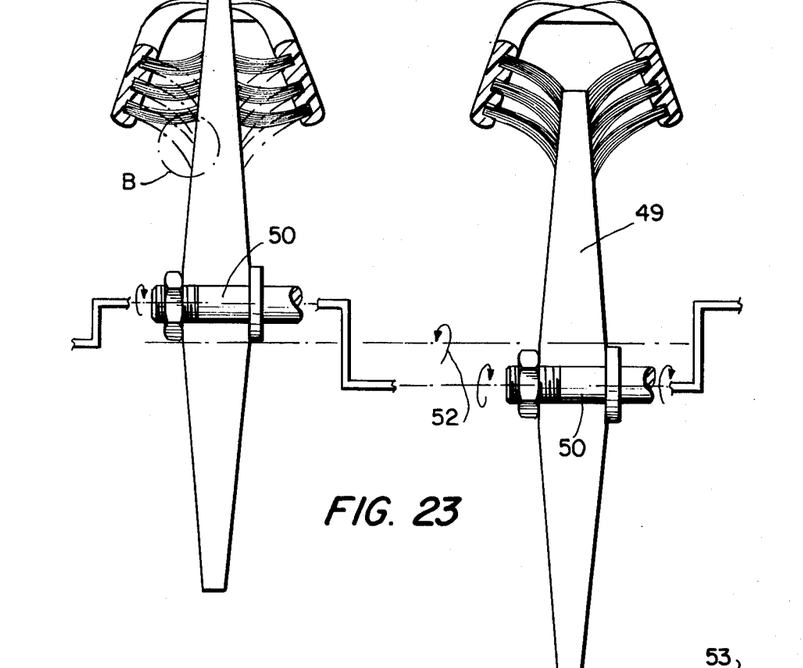
Figure 24:
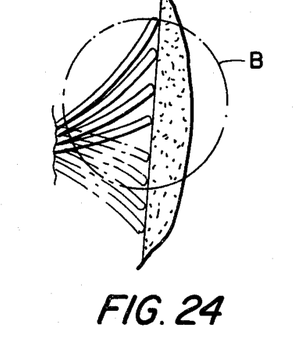
Figure 25:
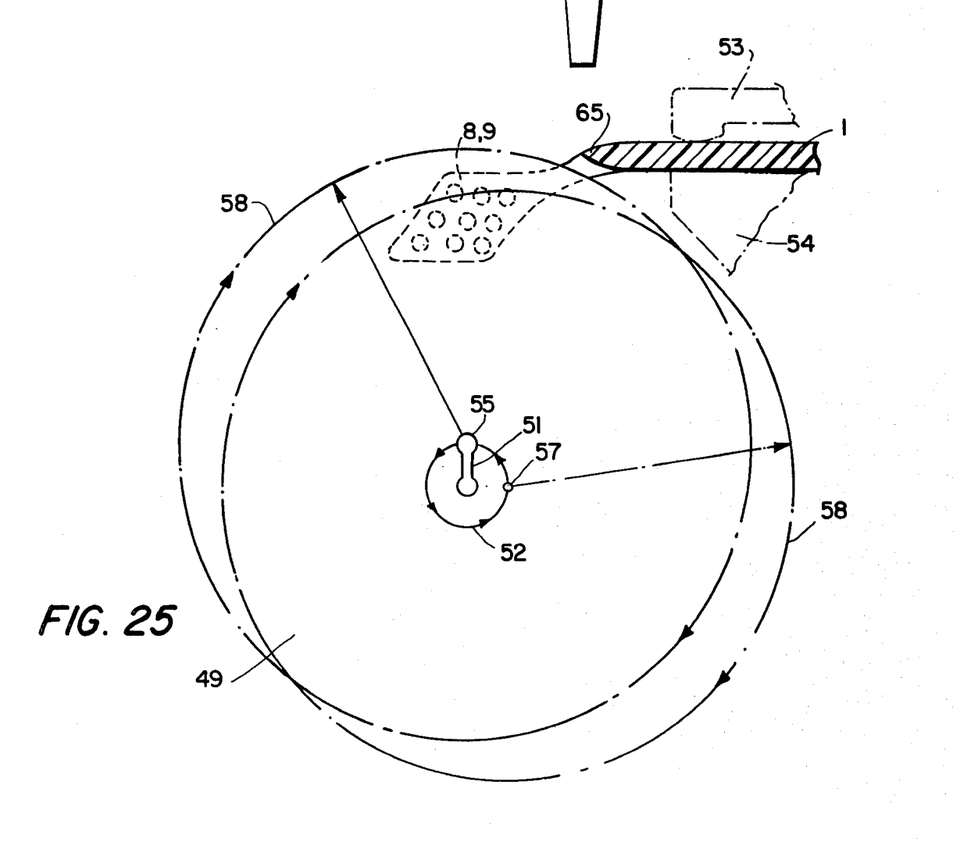

FIGS. 23 and 24 show a device suitable for rounding off the bristle ends and which can be used after the shaping procedure discussed in relation to FIGS. 20 and 21. It contains a discus-like grinding wheel 49 somewhat thicker at its outer rim than the gap 16 and accordingly can be introduced with only slight bending of the bristle bundles 11 in the gap 16 (FIG. 23). The grinding wheel 49 is rotatable about its axis of rotation 50 which is guided by means of a schematically shown crank 51 or the like along a circular path 52 of which the center axis is parallel to the axis of rotation 50. As shown in FIG. 25, the handle 1 of the toothbrush is clamped between two clamping jaws 53,54. If accordingly during the grinding procedure the outer crank end should be at a point 55 (FIG. 25), then the outer rim of the grinding wheel moves along a circular path 56. If now the crank end has rotated by about 270° as far as a point 57, then the outer rim of the grinding wheel 49 will be moving along a circular path 58. The directions of rotation are indicated by arrows in each case. The detail B shown in FIG. 24 demonstrates that due to these rotational motions, the ends of the bristle bundles 11 also move along circular paths and therefore will be rounded off. FIG. 23 furthermore shows the extreme positions of the grinding wheel 49 resulting from the eccentric motion of the axis of rotation 50. Alternatively it is possible to eccentrically rotate the clamping jaws 53 and 54.

When the shaping procedure illustrated in FIGS. 20 and 21 is carried out on a molded article 60 which evinces a relatively thick end segment 61 as shown in FIG. 4 and from which issue correspondingly thick connection arms 62, then the upper parts of the connection arms 62 in FIG. 4 will stretched so much in the region of the bends while the lower parts in FIG. 4 on the other hand will upset so much that in the vicinity of the sites denoted by 63 in FIG. 4 there occur in particular surface cracks, corrugations, pleats and other undesired deformations, and no smooth surface is obtained. In addition a wide end segment 61 is undesirable on formal grounds. Lastly the presence of a thick end segment 61 introduces problems during softening because more time is needed for heating and no uniform softening of the segments to be shaped can be achieved. Accordingly the invention provides for chamfering the end segment at its side away from the handle 1 so as to obtain a knife blade shape at its end, that is, to provide it with a tapering 65 (FIGS. 1,3,11,25) which is approximately triangular in topview (FIGS. 1,11) and about wedge-shaped in cross-section (FIGS. 3,25). Due to this removal of material, which is appropriately provided for by the corresponding design of the injection mold at the molded article 28 (FIG. 11), the said problems otherwise incurred when bending or folding the connection arms are completely eliminated.

Another problem arises when shaping the connection arms 6,7 if both of these are bent or folded around the same axis that for instance in FIG. 2 might be located tightly underneath the lower side of the end segment 2 and in the center plane 12. As a consequence of such shaping one obtains on one hand a plump appearance of the toothbrush as seen from the front and on the other hand an undesired overall height of the brush head. In the invention therefore each connection arm 6,7 is bent or folded around its own axis 66 or 67 resp. (FIG. 2). In this manner a shapely appearance is achieved and in addition, other conditions being the same, an extremely low brush height is made possible. For that purpose the end segment 2 is heated especially in those areas 68 (FIG. 11), ie it is softened therein, which adjoin the connection arms 6,7, the bending beams 44,45 (FIGS. 20,21) being guided on corresponding cams. The bending beams 44,45 furthermore are floatingly supported in the direction of the arrows 69 (FIG. 21) so that excessive stretching of the connection arms 6,7 be prevented during the bending procedure.

The invention is not restricted to the embodiments described. This applies in construction especially to the design of the handle and of the bristle segments which may assume shapes other than those shown. For instance the handle 1 may be slightly bent and be provided at its rear end 3 with a connection for a drive means which automatically imparts a reciprocating motion along the lengthwise axis of the toothbrush or makes it pivot to and fro about an axis of rotation. When such drive means are used, is may be appropriate to provide the handle with a curvature in its forward section (U.S. Pat. No. 4,141,967). In this and in other instances with curved handles, the essential part of the lengthwise axis for the sizing and the position of the bristle segments is the center axis of the highest handle part essentially parallel to said lengthwise axis.

Again there are numerous variations with respect to manufacture. This applies particularly to the mounting of the bristles and to the processing steps described in relation to cutting and rounding-off the bristle ends. Again the shaping of the connection arms can be carried out using other than the described means. Moreover it is not mandatory to so design the molded article 28 that it comprises plane-parallel upper and lower surfaces corresponding to FIGS. 11 through 14, or that the inside surfaces 10 lie in one plane. Also it is possible to arrange the axes of the blind holes 29 and correspondingly also the bundles of bristles 11 obliquely to the inside surfaces 14. In this regard however it would be necessary in case the molded article were manufactured by injection-molding to use a mold allowing to pull out of the blind holes the pins forming them before the entire molded article 28 can be removed from the mold.

It may be further advantageous to implant the bristle segments with bristles of different properties. Illustratively and especially the row most to the right in FIG. 3 might consist of soft bristles, the center row of medium-hard bristles and the furthest left row of hard bristles in order to use the soft bristles on the gums and still achieve effective cleaning with the remaining bristles.

The parts of the connection arms 6,7 joined to the bristle segments are approximately straight and subtend an angle of 30° to 60° with the plane 14, whereas their parts joining the end segment are curved depending on the position and arrangement of the bristle segments. Also, the connection arms are so short that they do not permit in typical use with typical forces being applied any significant spreading or increase in spacing between the bristle segments transversely to the center plane 12 on the basis of elasticity. Again the connection arms are so short that the bristle segments are arranged tightly below the plane 14 and practically as a whole on that side of a conceptual boundary surface transverse to the center plane 12 between the connection arms and the bristle segments.

As shown by FIGS. 1 and 11, the upper and lower sides 21 and 22 of the bristle segments can form with the outer edges of the connection arms a U-shaped profile as seen in topview, which is connected at its lowest point with the handle 1. The inside surfaces 10 can deviate from the drawing by being slightly curved concavely or convexly. Correspondingly the gap 16 need not be bounded by plane side surfaces 17, as these can also be slightly curved convexly or concavely The expression "gable-, wedge- or V-shaped" is meant to cover all these possible embodiments. Lastly the width of the gap 16 at the widest spot is about four millimeters and at the narrowest spot about two to three millimeters, though it can be selected to be somewhat more or less depending on the flexibility of the bristles. Furthermore a gap 16 may be provided as a function of the bristle properties and of the desired cleaning or massaging effect for which contrary to FIG. 2 the side surfaces 17 are mutually parallel or so inclined to each other that their conceptual extensions intersect in a line located on that side of the gap which is away from the end segment 2 and which in FIG. 2 would lead to a point 18 below the gap.

We claim:

1. A toothbrush made of a thermoplastically deforming plastic comprising an elongate handle having a grip portion, a front end segment with a tapered portion directed away from the grip portion, a back end, an upper side, and a longitudinal axis, the handle having defined therethrough a first, center plane containing said longitudinal axis, a pair of bristle-bearing segments;

a plurality of bristle bundles mounted in said pair of bristle-bearing segments, each bundle having free ends of bristles, and a pair of short, thermoplastically shaped connection arms joining said pair of bristle-bearing segments to said front end segment at said tapered portion, said connection arms, bristle-bearing segments and handle forming a fork having two prongs, each prong containing one bristle-bearing segment and one connection arm, said prongs being located on opposite sides of said first center plane and substantially below a second center plane perpendicular to said first center plane and containing said longitudinal axis, said bristle-bearing segments having mutually facing inside surfaces sloping toward each other in a gable-manner, planar extensions of said inside surfaces intersecting above said upper side of said handle at a first angle of less than 55°, said plurality of bristle bundles being mounted on said inside surfaces, said free ends of said bristle bundles bounding a gap and defining side surfaces for contact in use with teeth, said side surfaces sloping in a gable-manner toward each other, planar extensions of said side surfaces intersecting above said gap at a second angle which is less than said first angle.

2. The toothbrush according to claim 1, wherein each of the connection arms is arcuately shaped by thermoplastic deformation.

3. The toothbrush according to either claim 1 or 23 wherein each bristle-bearing segment has a front edge subtending an acute angle with a line parallel to said longitudinal axis.

4. The toothbrush according to either claim 1 or 23 wherein each bristle-bearing segment has a back edge subtending an acute angle parallel to said longitudinal axis.

5. The toothbrush according to claim 3, wherein said acute angle is from 30° to 60°.

6. The toothbrush according to claim 4, wherein said acute angle is from 30° to 60°.

7. The toothbrush according to claim 3 wherein each bristle-bearing sigment has upper and lower edges parallel to said longitudinal axis.

8. The toothbrush according to claim 4, wherein each bristle-bearing segment has upper and lower edges parallel to said longitudinal axis.

9. The toothbrush according to either claim 1 or 23, wherein said bristle-bearing segments are diamond-shaped.

10. The toothbrush according to claim 1 wherein said first center plane is a plane of symmetry for both said bristle-bearing segments and said bristle bundles.

11. The toothbrush according to claim 1, having a height of less than 35 mm.

12. The toothbrush according to claim 1, having a width of less than 20 mm.

13. The toothbrush according to either claim 1 or 23 characterized in that it is made from a substantially simple, integral injection-molded piece with subsequent thermoplastic deformation of the connection arms.

14. The toothbrush according to claim 1, wherein said bristle bundles are fastened in several rows and columns to said inside surfaces, consecutive rows being staggered such that each bristle bundle in a partiular row is positioned adjacent a gap in the adjacent row.

15. The toothbrush according to claim 1, wherein said bristle bundles are fastened to said inside surfaces such that each four adjacent bundles are arranged at respective four corners of a diamond.

16. The toothbrush according to claim 1, wherein said second angle is less than 15°.

* * * * *